(12) United States Patent
Menke et al.

(10) Patent No.: US 9,562,842 B2
(45) Date of Patent: Feb. 7, 2017

(54) METHOD FOR DETERMINING A BUFFER EFFECT OF AN ACTIVATED CARBON FILTER

(71) Applicant: Dr. Ing. h.c. F. Porsche Aktiengesellschaft, Stuttgart (DE)

(72) Inventors: Andreas Menke, Vaihingen (DE); Arne Burger, Braunschweig (DE); Matthias Heberle, Stuttgart (DE)

(73) Assignee: DR. ING. H.C.F. PORSCHE AKTIENGESELLSCHAFT, Stuttgart (DE)

( * ) Notice: Subject to any disclaimer, the term of this patent is extended or adjusted under 35 U.S.C. 154(b) by 413 days.

(21) Appl. No.: 14/053,805

(22) Filed: Oct. 15, 2013

(65) Prior Publication Data

US 2014/0102178 A1  Apr. 17, 2014

(30) Foreign Application Priority Data

Oct. 16, 2012 (DE) .................. 10 2012 109 842

(51) Int. Cl.
*G01N 15/08* (2006.01)
*F02M 25/08* (2006.01)

(52) U.S. Cl.
CPC ........... *G01N 15/082* (2013.01); *F02M 25/08* (2013.01); *F02M 25/089* (2013.01); *G01N 15/08* (2013.01); *G01N 2015/0866* (2013.01)

(58) Field of Classification Search
CPC ............ Y02T 10/7005; H01M 10/625; H01M 2220/20; H01M 10/613; H01M 2/1077; G01N 15/082

USPC ............................................................. 73/38
See application file for complete search history.

(56) References Cited

U.S. PATENT DOCUMENTS

| | | | | |
|---|---|---|---|---|
| 5,533,331 A | * | 7/1996 | Campbell | ............... B64G 1/26 60/204 |
| 5,558,068 A | * | 9/1996 | Kunishima | ........... F02D 33/006 123/179.17 |
| 6,692,634 B1 | * | 2/2004 | Yakovlevich | .......... C10G 27/14 208/133 |

(Continued)

FOREIGN PATENT DOCUMENTS

| | | | | |
|---|---|---|---|---|
| DE | 19619620 | 11/1997 | | |
| DE | 102008011453 | 9/2009 | | |
| DE | 102008011453 A1 | * 9/2009 | .......... G01M 99/008 | |

*Primary Examiner* — Eric S McCall
*Assistant Examiner* — Mohammed E Keramet-Amircolai
(74) *Attorney, Agent, or Firm* — Gerald E. Hespos; Michael J. Porco; Matthew T. Hespos

(57) ABSTRACT

A method for determining a buffer effect of an activated carbon filter for a tank venting system of a fuel container for hydrocarbon-containing fuels involves feeding a defined quantity of hydrocarbon molecules to the activated carbon filter (320) via a tank connection (320_1) of the activated carbon filter (320) by a hydrocarbon feed system (310). A carrier gas flow is introduced into the activated carbon filter (320) via an air connection (320_2) of the activated carbon filter (320), and a defined volumetric flow is sucked out of the activated carbon filter (320) via an engine connection (320_3) of the activated carbon filter (320) by a hydrocarbon measuring device (340), and its content of hydrocarbon molecules is measured. The defined quantity of hydrocarbon molecules is made available by the hydrocarbon feed system (310) in the form of a thermodynamically isolated gas quantity.

11 Claims, 3 Drawing Sheets

(56) References Cited

U.S. PATENT DOCUMENTS

| | | |
|---|---|---|
| 7,055,514 B2 | 6/2006 | Hannbeck Von Hanwehr et al. |
| 8,529,659 B2 | 9/2013 | Streib et al. |
| 2005/0193743 A1* | 9/2005 | Foss .................... C21D 1/62 |
| | | 62/50.2 |
| 2007/0103646 A1* | 5/2007 | Young .................. G01J 1/32 |
| | | 353/52 |
| 2011/0100210 A1* | 5/2011 | Streib ............... F02M 25/0809 |
| | | 95/11 |
| 2012/0060935 A1* | 3/2012 | Carter .............. F02M 21/0221 |
| | | 137/14 |

* cited by examiner

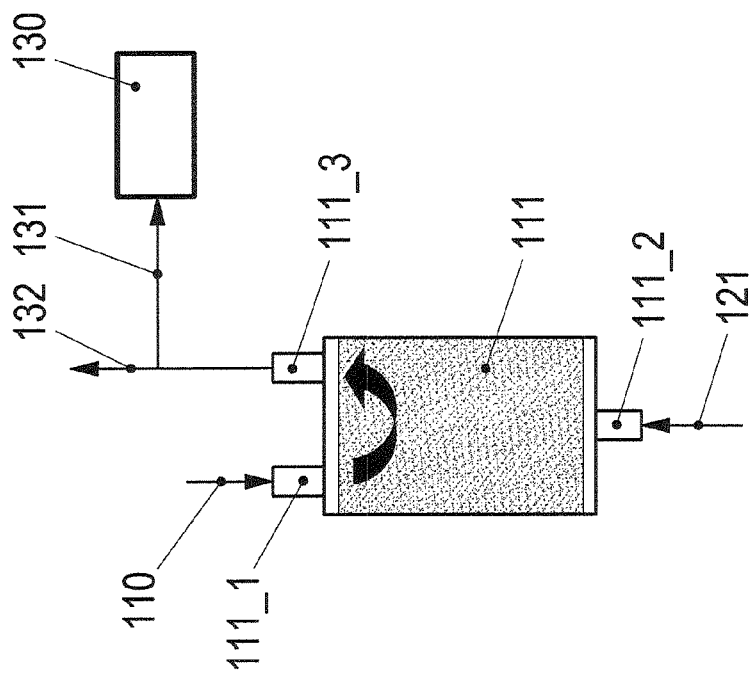
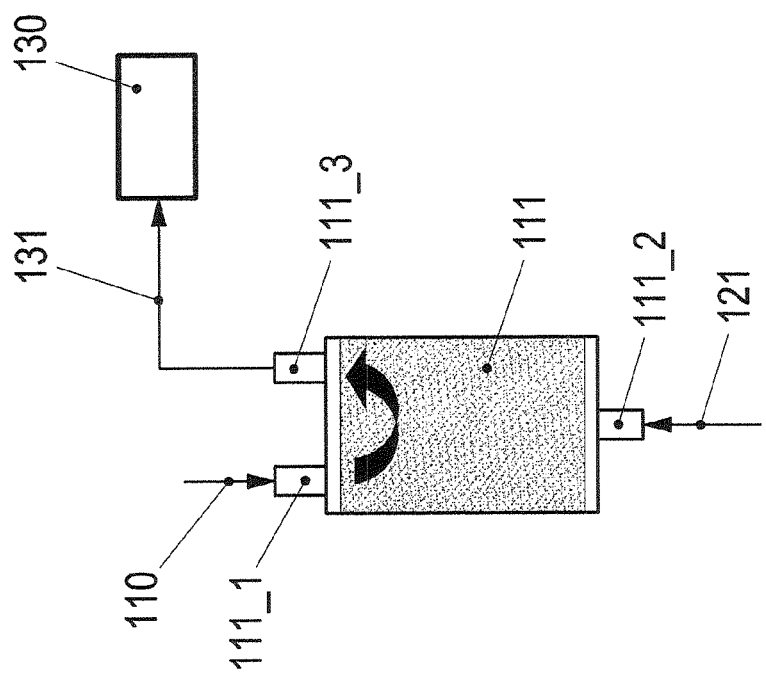

METHOD FOR DETERMINING A BUFFER EFFECT OF AN ACTIVATED CARBON FILTER

CROSS REFERENCE TO RELATED APPLICATION

This application claims priority under 35 USC 119 to German Patent Appl. No. 10 2012 109 842.5 filed on Oct. 16, 2012, the entire disclosure of which is incorporated herein by reference.

BACKGROUND

1. Field of the Invention

The invention relates to a method for determining a buffer effect of an activated carbon filter for a tank venting system of a fuel container for hydrocarbon-containing fuels. The invention also relates to a test bench and a hydrocarbon feed system for a test bench for determining a buffer effect of an activated carbon filter.

2. Description of the Related Art

Vehicles that have an internal combustion engine for burning hydrocarbon-containing fuels also have a tank venting system with an activated carbon filter between a corresponding fuel container and the surroundings. The activated carbon filter stores hydrocarbons, but must be regenerated periodically by an air flow under the control of an engine electronics system. In this context, air supplied to the activated carbon filter releases hydrocarbon molecules and transports those molecules to the engine. Hydrocarbon molecules in this air flow mix with the combustion air and are burned in the engine.

The tank venting system is intended to avoid an excess pressure in a fuel tank of a motor vehicle, for example in the event of the vehicle being subjected to increased solar radiation in the deactivated state. The activated carbon filter in the tank venting system prevents hydrocarbons from passing from the tank into the surroundings when pressure equalization is necessary. The air flow typically is sucked in by an underpressure in the intake manifold of the engine and functions as a scavenging gas that is fed with the released hydrocarbons to combustion spaces of the engine.

Modern internal combustion engines have an exhaust-gas-side lambda controller, and an increased hydrocarbon content in the fresh gas can disadvantageously affect the engine controller. The scavenging gas flow for regenerating the activated carbon filter therefore has to be set selectively so that only a comparatively small hydrocarbon quantity is fed to the fresh gas of the engine, with this quantity ideally being known or compensated for by the engine controller. A buffer effect can be detected during the scavenging of the activated carbon filter that is loaded with hydrocarbon molecules since the embedded hydrocarbon molecules are not all simultaneously given up to the scavenging gas, but instead are released gradually in the course of a scavenging gas flow process which lasts for a relatively long time. The scavenging gas flow should be as small as possible to avoid disadvantageous effects at the engine controller. At the same time, the scavenging gas flow should be as large as possible so that the regeneration of the activated carbon filter can be carried out as quickly and completely as possible to prepare the tank venting system for the next stationary state of the vehicle. The attempt to find an optimum scavenging gas flow generally fails due to the fact that the buffer effect of the respective activated carbon filter can be determined only with difficulty and is different for each type of activated carbon filter.

An object of the invention is to determine the corresponding buffer effect directly and comparatively easily for any type of activated carbon filter.

SUMMARY OF THE INVENTION

The invention relates to a method for determining a buffer effect of an activated carbon filter for a tank venting system of a fuel container for hydrocarbon-containing fuels. The method comprises feeding a defined quantity of hydrocarbon molecules to the activated carbon filter via a tank connection of the activated carbon filter by means of a hydrocarbon feed system. The method then includes introducing a defined carrier gas flow into the activated carbon filter via an air connection of the activated carbon filter by means of a carrier gas feed device. The method proceeds by sucking out the volumetric flow out of the activated carbon filter via an engine connection of the activated carbon filter by means of a hydrocarbon measuring device, and measuring the content of hydrocarbon molecules. The method makes the defined quantity of hydrocarbon molecules available by the hydrocarbon feed system in the form of a thermodynamically isolated gas quantity.

The hydrocarbon feed system initially stores the defined quantity of hydrocarbon molecules in a suitable way in preparation for feeding the defined quantity of hydrocarbon molecules, and makes the stored hydrocarbon molecules available when necessary for feeding to the activated carbon filter. The fact that the defined quantity of hydrocarbon molecules is made available in the form of a thermodynamically isolated gas quantity means that the gas quantity which is made available autonomously, i.e. independently of supply sources or feed lines or filling valves. The gas quantity that is made available already is stored in a thermodynamically isolated form in the hydrocarbon feed system before being fed to the activated carbon filter.

Thermodynamically isolated is intended to mean that the defined quantity of hydrocarbon molecules is made available as a quantity that is thermodynamically independent from the outside, and the volume, pressure and temperature are predefined and specified for the gas quantity that is made available.

A check valve connects a hydrocarbon source to a pressure control valve that is coupled to at least one container with a defined volume. The check valve is opened to make the defined quantity of hydrocarbon molecules available. The container is filled with hydrocarbon molecules at a defined pressure that can be set at the pressure control valve. As a result, a gas quantity is made available with a defined volume and a defined pressure.

The at least one container preferably is filled with hydrocarbon molecules at a defined, previously known temperature. The temperature may be an ambient temperature that can be measured and is therefore known.

At least two separate containers of different respective fixed volumes may be provided. Additionally, a changeover valve may be arranged between the pressure control valve and the at least two separate containers for optionally filling the containers. Thus, the hydrocarbon feed system comprises a hydrocarbon source, such as a butane gas bottle, that is connected to a pressure control valve via a check valve. A changeover valve is arranged downstream of the pressure control valve to optionally fill the separate pressure containers. The separate pressure containers have different fixed volumes. To fill a pressure container, a predefined desired container pressure initially is set at the pressure control valve. The changeover valve then is operated to select the desired pressure container. The check valve then is opened to allow gas, i.e. hydrocarbon molecules, to flow out of the hydrocarbon source into the selected pressure container. Therefore, gas quantities with a defined volume, corresponding to the respective volume of a pressure container, and a defined pressure, corresponding to the respective pressure set at the pressure control valve, are subsequently present, corresponding to the number of pressure containers.

A filling valve may be arranged at the tank connection of the activated carbon filter, and the defined quantity of hydrocarbon molecules is introduced into the activated carbon filter by opening the filling valve. If plural containers are provided, the changeover valve can select the container from which the correspondingly defined quantity of hydrocarbon molecules is to be introduced into the activated carbon filter.

As a result, a defined gas surge, corresponding to the defined quantity of hydrocarbon molecules, can be applied to the activated carbon filter. Real conditions under which the activated carbon filter is to be used can be modeled as closely as possible via the method of the invention. Thus, by specifying the quantities of hydrocarbon molecules that are made available in the hydrocarbon feed system, those quantities that also would be fed to the activated carbon filter in a real case, i.e. when the activated carbon filter is used in a motor vehicle, for example when pressure equalization is necessary, can be predefined in advance. In this context, three different quantities of hydrocarbon molecules that would be fed to an activated carbon filter of a motor vehicle in a real case may be stored in the hydrocarbon feed system as predefined quantities, can be predefined on the basis of empirical values. These are preferably a first quantity of 100 ml at 40 hPa excess pressure, a second quantity of 100 ml at 120 hPa and a third quantity of 300 ml at 450 hPa. These three differentiated quantities of hydrocarbon molecules make it possible to use only two different pressure containers, with one volume of 100 ml being made available for one pressure container, and one volume of 300 ml being made available for a second pressure container. To differentiate the first two specified quantities, all that is necessary is to change the pressure by the pressure control valve. As a result, a relatively simply designed hydrocarbon feed system permits differentiated and stable quantities of hydrocarbon molecules to be fed to the activated carbon filter to be tested so that a measurement or determination of its buffer effect to be carried out.

A time period of approximately 2 min is necessary to make available a predefined quantity of hydrocarbon molecules. The time period of approximately 2 min corresponds here to a cycle time, i.e. a time period of filling the at least one pressure container until the quantity of hydrocarbon molecules stored therein is discharged to the tank connection of the activated carbon filter.

A chronological profile of the content of hydrocarbon molecules of the defined volumetric flow that is sucked out of the activated carbon filter may be sensed and used as a correlation variable for the buffer effect of the activated carbon filter.

A defined nitrogen flow may be supplied as a carrier gas flow to the activated carbon filter by means of the carrier gas feed device.

The hydrocarbon concentration is to be measured in the scavenging flow, (see also DE 102008011453). The defined volumetric flow that is sucked out of the activated carbon filter by the hydrocarbon measuring device forms only part of a scavenging flow, comparable to the CVS in the exhaust gas measuring technology, that is sucked out of the activated carbon filter altogether via the hydrocarbon measuring device and an extraction device. The extraction device is coupled to the activated carbon filter via an extraction valve. Thus, the entire scavenging flow that is sucked out of the activated carbon filter is not fed to the hydrocarbon measuring device, but instead only a defined volumetric flow that branches off from the scavenging flow is fed in.

The invention also relates to a test bench for carrying out the method according to the invention.

The invention further provides a hydrocarbon feed system for a test bench for determining a buffer effect of an activated carbon filter for a tank venting system of a fuel container for hydrocarbon-containing fuels.

To introduce a defined quantity of hydrocarbon molecules into the activated carbon filter, the hydrocarbon feed system of the invention can be connected to the activated carbon filter via a tank connection of the activated carbon filter. In this context, the hydrocarbon feed system makes available the defined quantity of hydrocarbon molecules in the form of a thermodynamically isolated gas quantity.

The defined quantity of hydrocarbon molecules may be made available by connecting a hydrocarbon source via a check valve to a pressure control valve that is coupled to at least one container with a defined volume. Thus, by opening the check valve, the at least one container can be filled with hydrocarbon molecules at a pressure that can be set at the pressure control valve and is therefore defined. As a result, a quantity is made available with a defined volume and a defined pressure.

The at least one container can be filled with hydrocarbon molecules at a defined temperature.

At least two separate containers that have different fixed volumes may be provided. In addition, a changeover valve for optionally filling the separate containers may be arranged between the pressure control valve and the separate containers.

The hydrocarbon feed system according to the invention is configured for use for a test bench for carrying out a method according to the invention.

Further refinements and features of the invention can be found in the description and the appended drawing. The features specified above and explained below can be used in the respectively specified combination and also in other combinations or alone, without departing from the scope of the present invention.

BRIEF DESCRIPTION OF THE DRAWINGS

FIG. 2a and FIG. 2b illustrate various measuring methods for determining a buffer effect of an activated carbon filter.

DETAILED DESCRIPTION OF THE PREFERRED EMBODIMENTS

Figure 1:
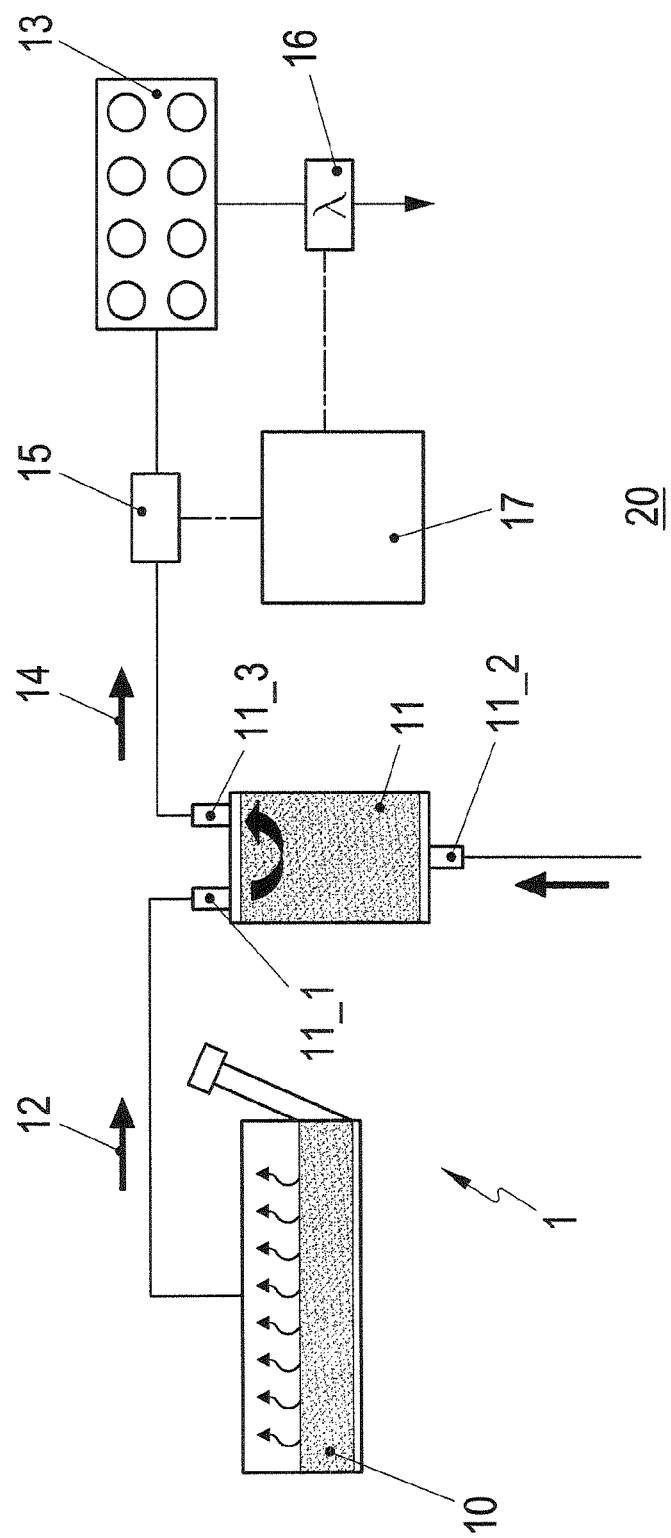
FIG. 1 is a schematic illustration of a tank venting system in a motor vehicle.

FIG. 1 shows a schematic illustration of a design of a tank venting system 1 in a motor vehicle. The tank venting system 1 can be used in a motor vehicle with a fuel tank 10 for hydrocarbon-containing fuels and functions to avoid an excess pressure in a fuel tank 10, such as when the motor vehicle is subjected to high solar radiation in an inactivate state. The tank venting system 1 has an activated carbon filter 11 to prevent hydrocarbons from passing from the tank 10 into the surroundings 20 during the pressure equalization. The hydrocarbons are supplied to the activated carbon filter 11 via a tank connection 11_1, as indicated by the arrow 12, and in the process are absorbed, that is to say stored, in the activated carbon filter 11. The activated carbon filter 11 can be scavenged with air and regenerated. The air for this purpose is sucked in from the surroundings 20 via an air connection 11_2 of the tank venting system 1 and is passed through the activated carbon filter 11 so that the embedded hydrocarbons are desorbed. The scavenging gas flow is sucked in by an underpressure in the intake manifold of the engine 13. As a result, the scavenging gas is fed with the released hydrocarbons to combustion spaces of the engine 13, as indicated by the arrow 14. The supply to the engine 13 is controlled by a regeneration and tank venting valve 15 that functions as a metering valve to control the scavenging gas flow in the direction of the engine 13. The tank venting valve 15 defines the extent of the scavenging gas flow that is fed to the engine 13. Suction caused by underpressure at the engine 13 when the tank venting valve 15 is open generates a carrier gas flow into the activated carbon filter 11 via the air inlet 11_2 and causes the hydrocarbon molecules to be desorbed. An exhaust-gas-side lambda controller 16 compares the ratio of the air to fuel with a stoichiometric mixture. The scavenging gas flow that contains hydrocarbon molecules can disadvantageously affect the engine controller 17. Therefore, a scavenging gas flow for regenerating the activated carbon filter 11 must be set so that comparatively low hydrocarbon quantities are fed to the fresh gas of the engine 13, with the hydrocarbon quantities being known or at least be compensated for at the engine controller 17. A buffer effect can be detected when the activated carbon filter 11 that is loaded with hydrocarbon molecules is being scavenged. More particularly, the embedded hydrocarbon molecules are not all output simultaneously to the scavenging air, but instead are desorbed gradually in the course of a scavenging gas or scavenging air flow process, which lasts for a relatively long time. The scavenging gas flow 14 is to be as small as possible to avoid disadvantageous effects at the engine controller 17. However, the scavenging gas flow 14 also should be as large as possible so that the regeneration of the activated carbon filter 11 can be carried out as quickly and completely as possible to prepare the tank venting system 1 for the next stationary state of the vehicle. The buffer effect of the respective activated carbon filter 11 must be known here or at least approximately estimated to determine an optimum scavenging gas flow.

FIG. 2a shows a highly simplified, circuit-diagram-like basic illustration of a test bench for carrying out a method for determining a buffer effect of an activated carbon filter 111. A defined hydrocarbon quantity 110 is fed to the activated carbon filter 111 by a hydrocarbon feed device via a tank connection 111_1 of the activated carbon filter 111. The tank connection 111_1 connects the activated carbon filter 111 to a fuel tank that is to be vented. The activated carbon filter 111 also has an engine connection 111_3, to which a hydrocarbon measuring device 130 is connected via a suction line 131. The hydrocarbon measuring device 130 is configured to suck a defined volumetric flow out of the activated carbon filter 111. In addition, the hydrocarbon measuring device 130 is configured to measure the hydrocarbon content in the volumetric flow that is sucked out of the activated carbon filter 111. The hydrocarbon measuring device 130 can be, for example, a flame ionization detector.

The activated carbon filter 111 also has an air connection 111_2 via which a carrier gas flow can be fed to the activated carbon filter 111. The carrier gas flow desorbs hydrocarbon molecules that have been deposited in the activated carbon filter 111 and carries those desorbed hydrocarbon molecules from the activated carbon filter 111 to the hydrocarbon measuring device 130.

The hydrocarbon quantity that is fed to the activated carbon filter 111 via a feed line is indicated symbolically in FIG. 2a by an arrow 110. The volumetric flow that is sucked out of the activated carbon filter 111 via the suction line is indicated in FIG. 2a by an 131. A further arrow 121 denotes the air quantity that continues to flow into the activated carbon filter 111 via a surroundings connection or air connection 111_2 of the activated carbon filter 111 from surroundings of the test bench. The hydrocarbon feed device expediently comprises a hydrocarbon source that is configured to provide a suitable hydrocarbon in a gaseous form and under pressure. For example, butane gas can be used as the hydrocarbon. From the prior art it is known that butane gas is made available in a corresponding butane gas bottle, in particular as a liquid gas.

The method for determining a buffer effect of the activated carbon filter 111 in the configuration illustrated in FIG. 2a also is denoted below as method I, and carried out as follows. Hydrocarbon is fed via the tank connection 111_1 to the activated carbon filter 111 from the hydrocarbon source via a throttle valve. Furthermore, a defined volumetric flow is sucked out of the activated carbon filter 111 via the engine connection 111_3 using the hydrocarbon measuring device 130. At the same time, the hydrocarbon content of this volumetric flow is measured. Furthermore, the chronological profile of the hydrocarbon content is detected and stored or correspondingly documented. This chronological profile of the measured hydrocarbon content then can be used as a correlation variable for the buffer effect of the activated carbon filter 111. At the start of the method, the activated carbon filter is regenerated or unloaded and therefore contains only a very small quantity of hydrocarbons. The hydrocarbons that are fed in via the hydrocarbon feed device can become embedded in the activated carbon filter 111. At the same time, the extraction of the volumetric flow brings about scavenging of the activated carbon filter 111, by which hydrocarbons are released from the activated carbon filter 111. Different buffer effects of different activated carbon filters 111 are already apparent from the fact that the chronological profile of the hydrocarbon content in the volumetric flow depends on the type of activated carbon filter 111 and the buffer effect thereof. Thus, different activated carbon filters 111 can be compared with one another or with respect to a reference activated carbon filter in terms of their buffer effect. In the measuring method shown here, the measuring device 130 also can suck in a constant volumetric flow of, for example, 200 l/h. During comparative measurements, the hydrocarbon quantity can be set so that the value of a previously measured reference activated carbon filter 111 is reached again. This permits comparative measurements with respect to a reference activated carbon filter to be implemented. During reference measurements of this type, the precise setting of the respective reference measured value is necessary before each measuring series begins, since different factors, such as, for example, the air pressure and the surrounding temperature, influence the measurement. Owing to a constantly changing pressure in the butane gas bottle which serves as a hydrocarbon source and in the associated feed lines, a reference activated carbon filter must be used here with a known buffer effect, i.e. with a known profile of the measured hydrocarbon content to be able to set and correspondingly take into account the hydrocarbon feed conditions at each measurement.

FIG. 2b shows a test bench with a design that is similar to FIG. 2a. However, the test bench of FIG. 2b has a further extraction device to permit a volumetric flow 132 of carrier gas to be sucked out in addition to the flow achieved by the hydrocarbon measuring device 130 to implement the scavenging flow. The volumetric flow 132 is far above the flow that would be possible by merely providing the hydrocarbon measuring device 130. Thus, a relatively large extraction power is made available with the test bench of FIG. 2b so that a significantly larger carrier gas flow can be directed through the activated carbon filter. However, only a partial flow 131 of the carrier gas flow that is directed through the activated carbon filter 111 or of the scavenging flow that emerges on the engine side through the engine connection 111_1 is directed to the hydrocarbon measuring device 130. The carrier gas flow that is introduced via the air connection 111_2 can in this case be a nitrogen flow that flows into the activated carbon filter 111 at a speed of, for example, 20 l/min. As a result, gas surges that are to be introduced simultaneously via the tank connection 111_1 can be increased in terms of their quantity and intensity since more hydrocarbon molecules can be transported away again by the relatively large carrier gas flow. The method that is applied for separating off a partial flow from the scavenging flow is referred to as a CVS (Constant Volume Standard) method. This method allows gas surges that are close to those in reality to pass into the tank connection 111_1 of the activated carbon filter 111, specifically gas surges such as those that occur in a real case of a tank venting system in a motor vehicle. In the text which follows, the respective methods for determining the buffer effect of an activated carbon filter in the case of such gas surges that are close to those in reality are denoted as method II and method III and will be explained in more detail below.

Figure 3:
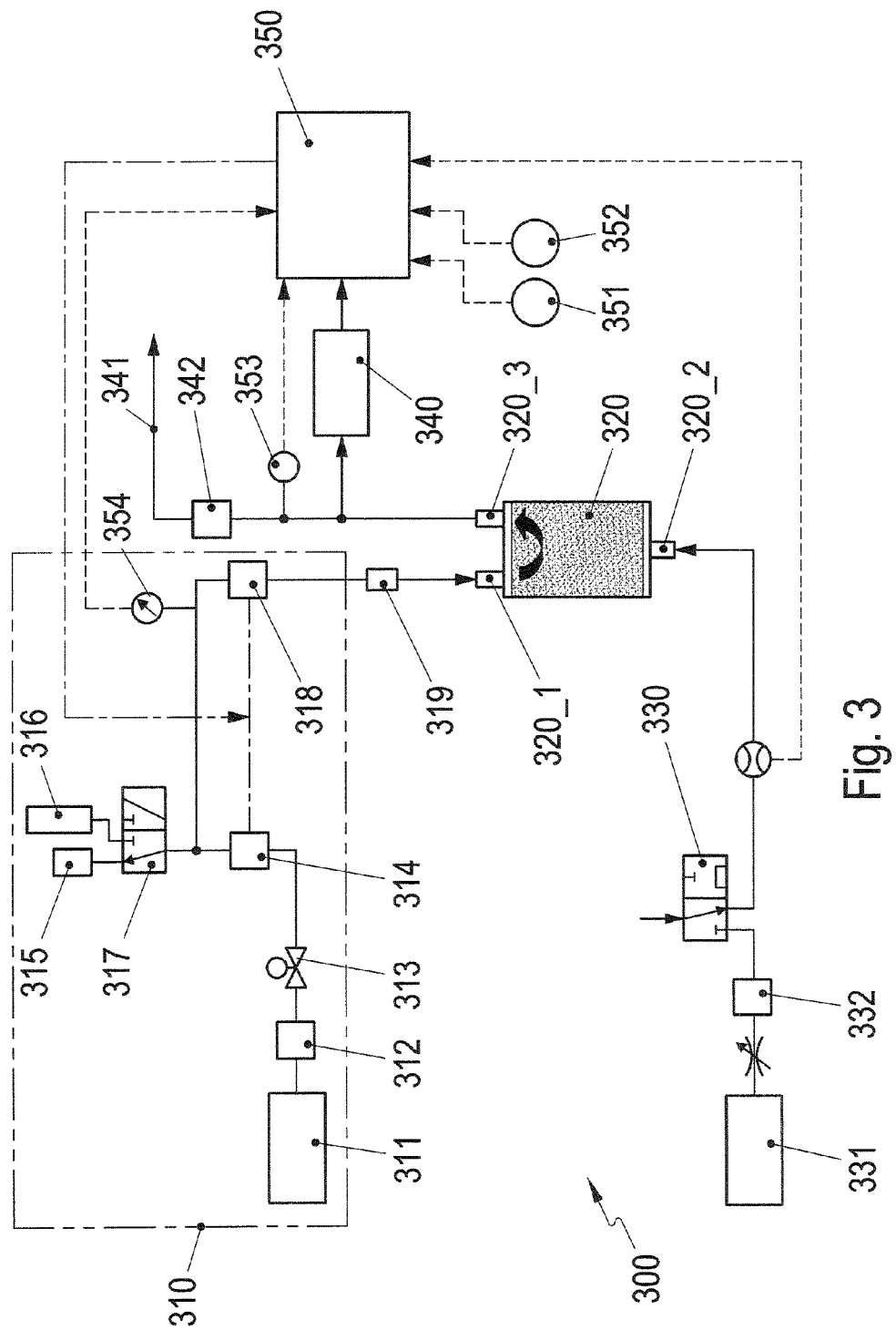
FIG. 3 is a schematic illustration of a design of an embodiment of the test bench according to the invention such as can be used to carry out the invention.

FIG. 3 is a schematic illustration of a test bench 300 that can implement the above-described methods I and II as well as the method III. The test bench 300 has a hydrocarbon feed system 310 that comprises a hydrocarbon source 311, such as a butane bottle where the butane gas is present as a liquid gas. The hydrocarbon source 311 is coupled to a check valve 312 that can be connected to a pressure container 315 via a pressure control valve 313 and a filling valve 314, or to a pressure container 316 via a changeover valve 317. The changeover valve 317 is used to select which of the pressure containers 315 or 316 is to be filled to store a defined quantity of hydrocarbon molecules in the hydrocarbon feed system 310 and to make it available for feeding to an activated carbon filter 320. The pressure control valve 313 is used to set the pressure with which the hydrocarbon gas is to be filled into the selected pressure container 315 or 316. Each of the pressure containers 315 and 316 has a fixed volume, and, as shown schematically, the pressure container 315 has a lower volume than the pressure container 136. The volumes may be, for example, a volume of 100 ml or 300 ml. At the set pressures, as a rule there is a volume of 100 ml at optionally 40 hPa or 120 hPa excess pressure when the relatively small pressure container, namely the pressure container 315, is filled. If the relatively large pressure container 316 is used with a volume of, for example, 300 ml, a pressure of approximately 450 hPa is used. As a result, when the check valve 312 is opened, the respectively selected pressure container can be filled with hydrocarbon gas via the filling valve 314, in such a way that the hydrocarbon gas present therein is at the pressure previously set at the pressure control valve 313. As a result, the pressure container 315 or 316 that is filled with hydrocarbon gas makes available a defined quantity of hydrocarbon molecules in the form of a thermodynamically isolated gas quantity. Thus, a permanently predefined volume, a permanently predefined pressure and, in addition, a permanently predefined temperature are provided for this gas quantity. The hydrocarbon feed system 310 enables the storage of predefined autonomous gas quantities, along with the feeding of those quantities into an activated carbon filter 320. The gas quantity that is to be fed to the activated carbon filter 320 therefore is no longer dependent on pressures that change in a hydrocarbon source or in corresponding feed lines, which is possible when there is a throttle valve. The hydrocarbon feed system of the invention can supply a hydrocarbon gas as a gas surge in a well defined, clocked fashion.

The hydrocarbon feed system 310 also enables automated feeding of a selectable gas surge to the activated carbon filter 320, and manual setting during the execution of the respective measuring methods is no longer necessary. The availability of corresponding gas quantities in the pressure containers 315 and 316 enables a measurement for determining a buffer effect of the activated carbon filter 320 to be carried out automatically. For this purpose, the hydrocarbon feed system 310 is coupled to the activated carbon filter 320 via a tank connection 320_1. A defined gas surge, specifically the precise gas quantity that is present in the selected pressure container can be fed to the activated carbon filter 320 via the tank connection 320_1, via a gas surge valve 318 and a hydrocarbon sensor 319. At the same time, a carrier gas flow is fed to the activated carbon filter 320 via an air connection 320_2. This may optionally involve, as described in FIG. 2, depending on the method selected, the feeding in of fresh air or else the feeding in of some other carrier gas, such as, for example, nitrogen. It is also possible to use a changeover valve 330 to select whether fresh air, i.e. air at atmospheric pressure, or a carrier gas, such as, for example, nitrogen, is fed in from a nitrogen source 331 via a throttle valve and a check valve 332 to the activated carbon filter 320 via the air connection 3202. In addition, a hydrocarbon measuring device 340 is provided at an engine connection 320_3 of the activated carbon filter 320 and can be a flame ionization detector. A further extraction device 341 is provided and can be connected or decoupled via an extraction valve 342. Depending on the selection of the measuring methods already explained in FIG. 2, the extraction device 341 is connected via the extraction valve 342, or only the extraction power of the hydrocarbon measuring device 340 is selected for sucking out a scavenging flow through the activated carbon filter 320.

According to measuring method I, only a comparatively small gas surge is fed to the activated carbon filter 320. This gas surge is removed from the relatively small pressure container 315, for example, at an excess pressure of approximately 40 hPa. Given this comparatively small gas surge, fresh air is fed in via the air connection 320_2, and only the extraction power of the hydrocarbon measuring device 340 is used at the engine connection 320_3. The hydrocarbon measuring device 340 can be a flame ionization detector. This means that the extraction valve 342 is closed here, and therefore the extraction device 341 is decoupled. The fresh air is sucked out, for example, at 90 l/h via the activated carbon filter 320.

In order to be able to carry out measuring method II or III, in the case of measuring method 2 the same relatively small pressure container 315 is selected, but here the gas is at a relatively high pressure, such as, for example, 120 hPa. For this purpose, in addition a carrier gas flow is selected from another carrier gas source, such as, for example, a nitrogen bottle 331, via the air connection 320_2, with the result that a carrier gas flow of 20 l/min can be made available here and the extraction power is greatly increased here by the extraction device 341 that is connected via the extraction valve 342. This suction power is increased greatly via the activated extraction device 341 and is closer to real conditions in terms of the suction power of a real engine. The hydrocarbon measuring device 340 is used as before to measure the hydrocarbon concentration and to determine the chronological profile of the hydrocarbon concentration. For this purpose a partial flow is removed or branched off from the sucked-out scavenging flow and is fed to the hydrocarbon measuring device 340.

The relatively large pressure container 316 is used when the measuring method III is carried out. The pressure container 316 can, for example, hold 300 ml at an excess pressure of 450 hPa.

The above-described measuring device or measuring arrangement enables mapping all regions that are close to the conditions in a real tank venting system in a motor vehicle. In addition, activated carbon filters can be characterized in terms of their buffer effect with respect to a reference activated carbon filter and in absolute terms.

Furthermore, the buffer effect of an activated carbon filter can be calculated by an equation with parameters that are determined from the conditions of the test bench. The test bench is not characterized by a reference activated carbon filter. The buffer effect can be specified and calculated as a defined variable characteristic of the respective activated carbon filter 320 in a computing unit 350 by using measured hydrocarbon concentration and the measured chronological profile of the hydrocarbon concentration as well as information on the ambient pressure 351, the ambient temperature 352, the extraction pressure or extraction suction 353 and the container pressure 354 of the container 315 or 316 that is selected for the respective measurement, to specify the.

In summary, the invention has the great advantage that calibration by reference measurement with a reference activated carbon filter can be dispensed with.

What is claimed is:

1. A method for determining a buffer effect of an activated carbon filter for a tank venting system of a fuel container for hydrocarbon-containing fuels, the method comprising: providing at least one thermodynamically isolated container with a defined volume; connecting a hydrocarbon source to a pressure control valve that is coupled to the at least one thermodynamically isolated container with the defined volume; filling the at least one thermodynamically isolated container with hydrocarbon at a pressure that can be set and defined at the pressure control valve and at a defined temperature for feeding a defined quantity of hydrocarbon molecules to the at least one thermodynamically isolated container; establishing gas flow communication between the thermodynamically isolated container and the activated carbon filter via a tank connection of the activated carbon filter by means of a hydrocarbon feed system; introducing a defined carrier gas flow into the activated carbon filter via an air connection of the activated carbon filter by means of a carrier gas feed device, thereby delivering the defined quantity of hydrocarbon molecules from the thermodynamically isolated container to the activated carbon filter; sucking a defined volumetric flow out of the activated carbon filter to a hydrocarbon measuring device; and measuring a content of hydrocarbon molecules in the defined volumetric flow out of the activated carbon filter.

2. The method of claim 1, wherein the at least one thermodynamically isolated container comprises at least two separate thermodynamically isolated containers that have different respective fixed volumes, the method further comprising operating a changeover valve between the pressure control valve and the at least two thermodynamically isolated or containers for optionally filling one of the containers.

3. The method of claim 1, further comprising opening a gas surge valve arranged at the tank connection of the activated carbon filter for introducing the defined quantity of hydrocarbon molecules into the activated carbon filter.

4. The method of claim 1, further comprising sensing a chronological profile of the content of hydrocarbon molecules of the defined volumetric flow that is sucked out of the activated carbon filter and using the sensed chronological profile as a correlation variable for the buffer effect of the activated carbon filter.

5. The method of claim 1, wherein the step of introducing a defined carrier gas flow into the activated carbon filter comprises supplying a defined nitrogen flow as the carrier gas flow to the activated carbon filter by the carrier gas feed device.

6. The method of claim 5, wherein the defined volumetric flow that is sucked out of the activated carbon filter by the hydrocarbon measuring device, forms a partial flow of a scavenging flow that is sucked out of the activated carbon filter via an extraction device.

7. The method of claim 6, wherein the extraction device is coupled to the activated carbon filter via an extraction valve.

8. A test bench for carrying out the method of claim 1.

9. A test bench for determining a buffer effect of an activated carbon filter for a tank venting system of a fuel container for hydrocarbon-containing fuels, the test bench including a hydrocarbon feed system connected to the activated carbon filter via a tank connection of the activated carbon filter, the hydrocarbon feed system comprising at least one thermodynamically isolated container with a defined volume; a hydrocarbon source connected via a check valve to a pressure control valve that is coupled to the at least one thermodynamically isolated container so that opening the check valve while setting a specified pressure at the pressure control valve fills the at least one thermodynamically isolated container with a defined quantity of hydrocarbon molecules in the form of a thermodynamically isolated gas quantity.

10. The test bench of claim 9, the at least one thermodynamically isolated container is temperature controlled to be filled with hydrocarbon molecules at a defined temperature.

11. The test bench of claim 9, wherein the at least one thermodynamically isolated container comprises at least two separate thermodynamically isolated containers that have different fixed volumes, and a changeover valve being arranged between the pressure control valve and the at least two containers for optionally filling a selected one of the containers.

* * * * *